United States Patent [19]
Beudeker et al.

[11] Patent Number: 6,017,530
[45] Date of Patent: Jan. 25, 2000

[54] PHOSPHOLIPASES IN ANIMAL FEED

[75] Inventors: Robert Franciscus Beudeker, Den Hoorn; Arie Karst Kies, Pijnacker, both of Netherlands

[73] Assignee: Gist-brocades, B.V., Netherlands

[21] Appl. No.: 08/648,506

[22] Filed: May 15, 1996

[30] Foreign Application Priority Data

May 15, 1995 [EP] European Pat. Off. .............. 95201266
Aug. 8, 1995 [EP] European Pat. Off. .............. 95202442

[51] Int. Cl.$^7$ .......................... A61K 38/46; A23K 1/165; C12N 9/18
[52] U.S. Cl. .......................... 424/94.6; 424/442; 435/197
[58] Field of Search ..................... 426/623, 635; 435/71.1, 71.2, 69.1, 195, 196, 197, 198, 252.3, 252.33, 254.11, 254.2, 254.21, 254.3; 800/205, 250; 424/94.6, 439, 442

[56] References Cited

U.S. PATENT DOCUMENTS 4,567,046  1/1986  Inoue et al. ............................... 426/20
5,759,537  7/1998  Garnett .................................. 424/93.43

FOREIGN PATENT DOCUMENTS

A 0 619 079  12/1994  European Pat. Off. .
A 0 635 574   1/1995  European Pat. Off. .
A 2 267 033  11/1993  United Kingdom .
WO 91/14772  10/1991  WIPO .

OTHER PUBLICATIONS

Trewavas et al. "Signal Transduction in Plants" Trends in Genetics 7(11–12): 356–361, Nov. 1991.
F. Korn–Wendish et al., "The Family Streptomycertaceae" in A. Balows et al, eds., *The Prokaryotes,* chapter 14, at pp. 950–951, 2nd edition, 1992.
N. Henderson, "Silage Additives", *Animal Feed Science and Technology,* 45, pp. 35–56, 1993.
Bennetzen et al., "The Primary Structure of the *Saccharomyces cerevisiae* Gene for Alcohol Dehydrogenase I" *Bio Chem* 257:3018–3025 (1982).

Geus et al., "Expression of porcine pancreatic phospholipase A$_2$. Generation of active enzyme by sequence–specific cleavage of a hybrid protein from *Escherichia coli*" *Nucl. Acid Res.* 15:3743–3759 (1987).
Ito H. et al., "Transformation of Inact Yeast Cells Treated with Alkali Cations" *J. Bacteriol* 153:163–168 (1983).
Reiss et al., "Protein fusions with the kanamycin resistance gene from transposon Tn5" Geneticin, BRL, *Embo J* 3:3317–3322 (1984).
Swinkels et al., "The yeast *Kluyveromyces lactis* as an efficient host for heterologous gene expression" *Antonie van Leeuwenhoek* 64:187–201 (1993).
van den Bergh et al., "Secretation of biologically active porcine prosphospholipase A$_2$ by *Saccharomyces cerevisiae*" *Eur J. Biochem* 170:241–246 (1987).
van den Berg et al., "*Kluyveromyces* as a Host for Heterologous Gene Expression: Expression and Secretion of Prochymosin" *Bio/Technol.* 8:135–139 (1990).
Weisbjert et al., "Digestibility of Fatty Acids in the Gastroinestinal Tract of Diary Cows Fed with Tallow of Saturated Fats Rich in Stearic Acid or Palmitic Acid" *Acta Agric. Scand. Section A, Animal Sciences* 42:114–120 (1992).

*Primary Examiner*—George C. Elliott
*Assistant Examiner*—Thomas G. Larsen
*Attorney, Agent, or Firm*—Morrison & Foerster, LLP

[57] ABSTRACT

The present invention discloses a process for improving the efficiency of feed utilization and/or for promoting the growth of animals in which an animal is fed a diet which comprises a composition comprising feed substance and a ready for use phospholipase additive. Preferably said composition also comprises at least one phospholipid. Said compositions are used to improve fat digestibility and to promote growth of the animal. The phospholipid is preferably lecithin and the preferred phospholipase is a mammalian phospholipase A2. In a preferred embodiment the phospholipase is produced using recombinant DNA technology to express the enzyme in a suitable host such as a microorganism or a transgenic plant.

19 Claims, No Drawings

SEQUENCE LISTING

<160> NUMBER OF SEQ ID NOS: 4

<210> SEQ ID NO 1
<211> LENGTH: 30
<212> TYPE: DNA
<213> ORGANISM: mammalian

<400> SEQUENCE: 1
tgtcatgccc gggcattatg gcagtttcgt          30

<210> SEQ ID NO 2

-continued

```
<211> LENGTH: 39
<212> TYPE: DNA
<213> ORGANISM: mammalian

<400> SEQUENCE: 2
agtcctcggt acctcgagtc agcagtactt cttggtgtc                           39

<210> SEQ ID NO 3
<211> LENGTH: 73
<212> TYPE: DNA
<213> ORGANISM: mammalian

<400> SEQUENCE: 3
tcgacaaaaa tgaaattcct cgtgttggct gttctgctca cagtgggcgc tgcccaggaa    60
    ggcatcagct caa                                                       73

<210> SEQ ID NO 4
<211> LENGTH: 69
<212> TYPE: DNA
<213> ORGANISM: mammalian

<400> SEQUENCE: 4
ttgagctgat gccttcctgg gcagcgccca ctgtgagcag aacagccaac acgaggaatt    60
    tcatttttg                                                            69
```

PHOSPHOLIPASES IN ANIMAL FEED

FIELD OF THE INVENTION

The present invention relates to the application of enzymes in feed for livestock.

BACKGROUND OF THE INVENTION

A number of enzymes are secreted in the gastrointestinal tract of animals to digest food. Each of these enzymes acts on specific components in a specific environment of a part of the gastrointestinal tract. Pepsins, for example, are active in the acidic environment of the stomach, whereas other proteases such as chymotrypsin and carboxypeptidases show activity in the upper part of the small intestine at pH 6–7. Many such enzymes need a precursor before being activated. Pepsin, for example, is only formed from pepsinogen in an acidic environment. Chymotrypsin and carboxypeptidases are both secreted in an inactive form and are activated by the protease trypsin.

The digestion of fat is a complex process. Most fat in diets for animals is available in the form of triglycerides. These triglycerides are hardly if at all absorbable by the intestine and need to be degraded to mono- and diglycerides, glycerol and free fatty acids. This conversion is catalyzed by the enzyme lipase which is secreted by the pancreas. This enzyme is active on the interface of water and oil. For good digestion it is essential to have very small droplets of fat in an oil-in-water emulsion. Emulsifiers are surface-active substances that allow the dispersion of fat in a water phase. The most important emulsifier in the gastrointestinal tract is bile. Bile is secreted by the liver and may be stored in the gall bladder. Bile contains a.o. bile acids and salts, cholesterol and phospholipids. Small particles, micelles, are formed by the mixture of the bile components with the (remaining) triglyceride products.

These micelles are diffused to the jejunal epithelial cells, where their contents are released and absorbed. In these epithelial cells, triglycerides are reconstituted. Together with cholesterol, cholesterol esters, phospholipids and proteins, they form new, water soluble, particles termed chylomicrons.

Phospholipids such as lecithin are enzymatically degraded by action of phospholipases A and B which are also secreted by the pancreas.

Lecithin is a mixture of both polar and neutral lipids in which the content of polar lipids is at least 60%. Because of their hydrophobic/hydrophillic character polar lipids (and thus lecithins) are used as emulsifiers. Polar lipids include (glycero)phospholipids and glycolipids. The basic structure of a glycerophospholipid is as follows:

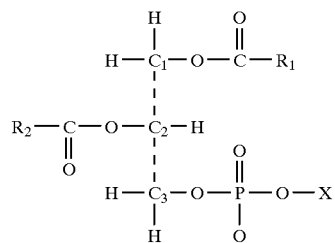

X = Choline
Ethanolamine
Inositol
Serine
Hydrogen

Glycerophospholipids basically consist of a glycerol moiety with fatty acids at the C1- and C2 position. The C3-position is esterified with phosphoric acid. This phosphoric acid is often linked with an alcohol group thus generating the following compounds:

phosphatidyl-ethanolamine (PE; X=ethanolamine)
phosphatidyl-choline (PC; X=choline)
phosphatidyl-serine (PS; X=serine)
phosphatidyl-inositol (PI; X=inositol)
phosphatidyl acid (PA; X=hydrogen)

Glycerophospholipids bearing just one (instead of the usual two) fatty acid residues are called lyso-phospholipids.

Lecithin is used as an emulsifier in numerous applications including food and feed. Emulsifiers are surface-active substances that allow the dispersion of an oil liquid phase in a water phase. Emulsifiers possess both hydrophillic and lipophilic groups within the same molecule. The ratio of hydrophillic to lipophilic groups, known as the HLB value, is a characteristic indicator for emulsifiers.

Fat-soluble hydrophobic emulsifiers have HLB values in the range of 0 to less than 10 while water-soluble compounds have HLB values between above 10 and 20.

Emulsifiers such as lecithin are added to animal feed to achieve an improved nutritive value of the feed or to achieve a better dispersion in the case of liquid feed. It is also known to add lysolecithin to animal feed (under the trade name Lysoforte® sold by the Kemin company) which has improved emulsifying properties leading to a better nutritive value (Pluimveehouderij 24: 20–21 (Mar. 18, 1994).

The emulsifying properties of lecithin are not only exploited in livestock production by inclusion of lecithin in dry rations but also in areas where animals are given liquid feed containing a large proportion of fat. These are primarily milk replacements for calves and sow milk substitutes for piglets. The function of lecithins is to produce the finest possible dispersion of the fat in the ready prepared liquid feed. The fine dispersion results in improved digestibility of the fat by the animals. In addition, the lecithin exhibits a favourable effect on the settling of insoluble constituents in a liquid feed.

In recent years, the feed industry has started to use industrially produced enzymes to complement enzymes produced in the gastrointestinal tract of the animals. Examples comprise phytases, α-amylases, proteases, and various plant cell wall degrading enzymes. However, nowhere in the prior art has the direct addition of phospholipases to animal feed for the purpose of promoting the growth of animals been described since the animals themselves already secrete large amounts of these enzymes in the upper part of the small intestine.

EP-A-0 619 079 discloses the use of inter alia phospholipids as coatings for granulates containing biologically active substances to be include in feed for ruminants. The coating serves to protect the biologically active substances in the rumen, in order to allow subsequent digestion and absorption thereof via the post-abomasum digestive organs. EP-A 0 619 079 further discloses that optionally a phospholipase can also be incorporated in the protective coatings in order to aid in their hydrolysis, however, EP-A 0 619 079 does not disclose or suggest that phospholipases can be added to feed in order to promote growth or to improve the efficiency of feed utilization.

GB-A-2 267 033 is concerned with promoting growth, however, GB-A-2 267 033 teaches to add a kit comprising the phospholipid lecithin together with a Streptomyces strain to silage. It was suggested that the Streptomyces strain is capable of producing a phospholipase A2 during fermentation of the silage. It follows that the use of said kit is limited to animal feed of which the production process comprises a fermentation stage which is compatible with phospholipase production by said Streptomyces strain. Hence, there is still a need for a widely applicable, versatile and ready-for-use phospholipase feed-additive for improvement of the efficiency of feed utilization and/or for the promotion of growth of animals.

SUMMARY OF THE INVENTION

The present invention provides a process for improving the efficiency of feed utilization in which an animal is fed a diet which comprises a composition comprising feed substance and a ready for use phospholipase additive.

The present also invention provides a process for promoting the growth of animals in which an animal is fed a diet which comprises a composition comprising feed substance and a ready for use phospholipase additive.

The invention further provides animal feed compositions comprising feed substance and a ready for use phospholipase additive.

In addition the invention provides a process for the production of an animal feed which comprises producing phospholipase recombinantly in a microorganism or a transgenic plant and mixing the phospholipase thus obtained with feed substance.

DETAILED DESCRIPTION OF THE INVENTION

The present invention discloses the use of exogenously added and ready for use phospholipases in feed for animals to improve the emulsifying properties of phospholipids in the gastrointestinal tract and thereby improving the efficiency of feed utilization and/or promoting the growth of the animal. Promoting the growth of animals is herein defined as promoting growth in terms of weight gain in time (growth rate) and/or promoting growth in terms of feed efficiency (feed conversion ratio).

Phospholipases which may be used in the invention include: phospholipase A1 (EC 3.1.1.32), phospholipase A2, phospholipase B (lysophospholipase), phospholipase C and phospholipase D.

Specifically, the present invention discloses the application of feed to which phospholipase A2 (EC 3.1.1.4) is added. Phospholipase A2 may be produced by isolation from e.g. porcine pancreas as a byproduct from e.g. insulin production. Alternatively, phospholipase A2 may be produced recombinantly by expression of a heterologous gene in a micro-organism such as e.g. *Kluyveromyces lactis*. The enzyme is obtained from such micro-organisms by means of fermentation and down-stream processing to recover the enzyme.

Another possibility for the exogenous addition of phospholipases to lecithin containing animal feed, is to add phospholipase containing transgenic plant materials, preferably transgenic seed, in which the phospholipase has been synthesized through heterologous gene expression. To obtain this the gene encoding the phospholipase is cloned in a plant expression vector, under control of the appropriate plant expression signals, e.g. a tissue specific promoter, such as a seed specific promoter. The expression vector containing the phospholipase gene is subsequently transformed into plant cells and transformed plant cells are selected for regeneration into whole plants. The thus obtained transgenic plants can be grown and harvested, and those parts of the plants containing the heterologous phospholipase, can be included in animal feed, either as such or after further processing. The heterologous phospholipase may be contained in the seed of the transgenic plants or it may be contained in other plant materials such as roots, stems, leaves, wood, flowers, bark, and/or fruit.

Thus a phospholipase additive is understood to mean a phospholipase which is not a natural constituent of the main feed substances or is not present at its natural concentration therein, e.g. the phospholipase is added to the feed separately from the feed substances, alone or in combination with other feed additives, or the phospholipase is an integral part of one of the feed substances but has been produced therein by recombinant DNA technology.

A ready for use phospholipase additive is herein defined as an additive that is not produced in situ in animal feed. A ready for use phospholipase additive may be fed to animals directly or, preferably, directly after mixing with other feed constituents. Ready for use phospholipase additives do include phospholipases that are in the inactive pro-form but that can be activated in the GI-tract, e.g. by proteolytic processing.

A preferred feed contains phospholipid, preferably lecithin as present in raw materials as for example either full fat soybeans, full fat rapeseed, soybean oil, rapeseed oil or any other oilseed or oil rich in lecithin in addition to the exogenously added phospholipase, which is preferably (microbially produced) porcine phospholipase A2. However, the feed does not need to comprise phospholipid as the pancreas already secretes phospholipid.

It is another aspect of this invention that phospholipase, preferably (microbially produced) porcine phospholipase A2, is included in milk replacers containing lecithin for young animals. This improves the digestibility of fat by young animals.

It is yet another aspect of this invention that a phospholipase is included in diets of fish and crustaceans in order to improve growth and feed conversion ratio.

Upon treatment with e.g. phospholipase A2 (PLA2), the HLB value of lecithin is raised from 7 to approximately 8 or 9 which may contribute to the beneficial effects of phospholipase A2 treatment on emulsification properties of lecithin.

Porcine phospholipase A2 exhibits no activity in vitro below pH 6.0. The prevailing pH in the GI-tract of monogastric animals is below 6.0 in the crop and stomach.

One would not expect any beneficial effect of the addition of phospholipase A2 since:

a) no activity is expected of an added phospholipase in the crop and stomach as a consequence of a mismatch between prevailing pH and pH dependency of the enzyme; and b) the animals themselves secrete large amounts of this enzyme in the upper part of the small intestine where the prevailing pH is in line with the pH dependency of the enzyme.

Surprisingly, it was found that the addition of exogenous porcine phospholipase A2 results in a markedly improved feed conversion ratio in broilers (Example 3).

Apart from monogastric animals, phospholipase A2 may also be used advantageously in polygastrics. During early lactation of high producing dairy cows for example, it is of interest to include high levels of fat in their diets to compensate in part for the large negative energy balance. From literature it is known that the digestibility of fatty acids in the GI-tract of dairy cows varies as a function of inter alia ration composition and source of fat. Digestibilities of fatty acids have been found to vary between 87% for a diet containing 500 g of saturated fat high in palmitic acid (C16:0) to 64% for a diet containing 1000 g of saturated fat high in stearic acid (C18:0) (Weisbjerg et al., Acta Agric. Scand. Section A, Animal Sciences 42 p. 115–120, 1992).

A large part of the variation in digestibility of fatty acids in dairy cows is explained by variations in digestibility in the small intestine (Ibid, p.114–120). Action of phospholipase A2 in the small intestine of dairy cows is likely to enhance the digestibility of fatty acids.

Proteins such as the enzyme phospholipase A2 are usually degraded rapidly in the rumen. As a consequence, these proteins should be delivered to the small intestine in a way that prevents degradation in the rumen. A number of formulation methods are available to persons skilled in the art to protect enzymes from inactivation in the rumen.

A significant improvement has also been found in fat digestibility by non-ruminating calves upon addition of phospholipase, specifically porcine phospholipase A2 (Example 4).

Diets for fish and crustaceans are also often supplemented with relatively high concentrations of phospholipids in order to achieve an acceptable growth, health and feed conversion. In accordance with the invention phospholipase may also be added to these diets to further improve growth and feed conversion ratio.

It is yet a further aspect of the invention that the addition of phospholipase, and optionally phospholipid, to animal feed allows to reduce the amounts of expensive feed ingredients, such as vitamines and/or colorants, to be incorporated in the feed.

Phospholipase may be added to feed in a concentration which varies as a function of type and concentration of phospholipid and target animal generally between about 1,000–5,000,000 international units (IU, for definition see Example 1) per kg of phospholipid. Preferably about 10,000–500,000 IU are added per kg of phospholipid. In general, animal feeds contain about 1–2 g of phospholipid per kg. Consequently, a range of 1–10,000 IU/kg, or preferably 10–1,000 IU/kg of feed will be appropriate, however, most preferred is a range of about 100–1,000 IU/kg feed. It follows that the dosage of phospholipase added to the feed can be adjusted in case of an unusual phospholipid content of the feed.

In a preferred embodiment of the invention the phospholipase is obtained using recombinant DNA technology. The phospholipase is recombinantly produced by heterologous expression of a phospholipase gene or cDNA in a suitable host organism or, alternatively, by homologous overexpression of a suitable endogenous gene.

The specific embodiments of the present invention described herein use porcine phospholipase A2 as produced by heterologous gene expression in the yeast *Kluyveromyces lactis*. However, the skilled person will understand that phospholipases obtained from other sources will also function in the present invention. Such phospholipases may be derived from other mammals such as e.g. rats, mice or humans, for all of which the phospholipase A2 genes are available in the art. Alternatively, the phospholipases may be derived from organisms other than mammals, such as e.g. microbial or even plant phospholipases.

Similarly, the microorganism used for the production of the phospholipase used in the invention is not necessarily limited to the yeast *Kluyveromyces lactis* only. Apart from *K.lactis*, successful heterologous expression of the porcine phospholipase A2 gene has been reported in *Escherichia coli*, *Saccharomyces cerevisiae* and *Aspergillus niger* (reviewed by Swinkels et al. 1993, Antonie van Leeuwenhoek 64, 187–201). It is therefore expected that successful (heterologous) expression of the phospholipases of the invention can be obtained in a wide range of microorganisms. Preferred microorganisms for this purpose are bacteria of the genera Bacillus and Escherichia, yeasts of the genera Saccharomyces, Kluyveromyces, Hansenula, Pichia, Yarrowia, Candida, or filamentous fungi of the genera Aspergillus, Fusarium, and Trichoderma.

Regarding the methods for expression of phospholipases in transgenic plant materials, preferably in seed, we refer to International Application WO 91/14772 which provides general and specific guidance for generating transgenic plants, and which discloses general methods for the (heterologous) expression of enzymes in plants, including methods for seed-specific expression of enzymes.

The skilled person will understand that addition of the phospholipase in the form transgenic plant material, e.g. transgenic seed containing the phospholipase, may require the processing of the plant material so as to make available the enzyme, or at least improve its availability. Such processing techniques may include various milling and grinding techniques or thermomechanical treatments such as extrusion or expansion.

The present invention is not limited to the use of Streptomyces strains capable of producing a phospholipase A2 during fermentation of silage, which inter alia provides the following advantages:

Any phospholipase can be included. This allows to use phospholipases which are endogenous to the animal in which the enzyme is to be applied, which will facilitate obtaining product-approval from the regulatory authorities This further allows to select a phospholipase most suited for application as feed additive.

The need to ferment the feed in order to produce the enzyme in situ is obviated. This allows to control precisely the amount of phospholipase additive in the feed, which is important in view of the optimum in the range phospholipase concentrations in certain applications (see Example 3).

It also allows great flexibility in the formulation of both the enzyme additive and the feed comprising the same.

The addition of mammalian phospholipase A2 provides an unexpectedly high effect on growth promotion.

The examples herein are given by way of illustration and are in no way intended to limit the scope of the present invention.

EXAMPLE 1

Expression of Porcine Phospholipase $A_2$ ($PLA_2$) in the Yeast *Kluyveromyces lactis*

The identification and molecular cloning of the gene encoding the porcine phospholipase $A_2$ protein is described in detail previously by de Geus et al. (Nucl. Acid Res. 15, 3743–3759, 1987) and van den Bergh et al. (Eur. J. Biochem 170, 241–246, 1987).

With one of these well characterized clones, pCB08T, containing the entire $PLA_2$ cDNA sequence and Kluyveromyces specific genetic regulatory elements, we constructed the expression-cassette pKLAPLA-11 in order to obtain expression of porcine $PLA_2$ in the yeast *Kluyveromyces lactis*. As the $PLA_2$ cDNA sequence and the sequences for the *K.lactis* regulatory elements are all available in public databases, the skilled person can obtain all materials required to construct expression-cassettes for the expression of $PLA_2$ in *K.lactis*.

All standard molecular cloning techniques such as isolation and purification of nucleic acids, electrophoresis of nucleic acids, enzymatic modification, cleavage and/or amplification of nucleic acids, transformation of E. coli, etc., were performed as described in the literature (Sambrook et al. (1989) "Molecular Cloning: a laboratory manual", Cold Spring Harbour Laboratories, Cold Spring Harbour, N.Y.; Innis et al. (eds.) (1990) and "PCR protocols, a guide to methods and applications" Academic Press, San Diego). Synthesis of oligo-deoxynucleotides and DNA sequence analysis were performed on Applied Biosystems 380B DNA synthesizer and 373A DNA sequencer, respectively, according to the user manuals supplied by the manufacturer.

To facilitate the construction of pKLAPLA-11 first appropriate flanking restriction sites were introduced at the borders of the mature PLAcDNA sequence by the Polymerase Chain Reaction (PCR). At the 5'-border, just at the cleavage site of the pro- and mature $PLA_2$ protein, a SmaI and at the 3'-border, just downstream the stop codon, XhoI and KpnI restriction sites were introduced, simultaneously. To do so, two oligo nucleotides were synthesized:

```
Oligomer 1
                        mature PLA₂
  5'TGT CAT GCC CGG GCA TTA TGG CAG CAG TTT CGT 3'
            SmaI Oligomer 2

5' AGT CCT CGG TAC CTC GAG TCA GCA CTA CTT CTT GGT GTC-3'
         KpnI    XhoI    stopcodon PLA₂
```

The PCR amplification was performed with oligomers 1 and 2 as primers and pCB08T as template. The obtained amplified 400 bp PLAcDNA fragment was digested with SmaI and KpnI and subsequently inserted into the appropriate sites of pTZ18R by molecular cloning. The resulting vector was designated pPLA-1. This modified PLAcDNA fragment was sequenced entirely to verify the PCR amplification reaction and the introduced flanking restriction sites.

To introduce a SalI restriction site and optimal yeast translation initiation sequences at the 5'-border of the prepro-signal sequence of $PLA_2$ two complementary synthetic oligo nucleotides were synthesized.

```
  SalI           SSpre
5'-TCG ACA AAA ▓▓▓ AAA TTC CTC GTG TTG GCT GTT CTG CTC ACA-
        GT TTT TAC TTT AAG GAG CAC AAC CGA CAA GAC GAG TGT- → proPLA₂
-GTG GGC GCT GCC CAG GAA GGC ATC AGC TCA A-3'
-CAC CCG CGA CGG GTC CTT CCG TAG TCG AGT T-5'
```

After annealing these two oligomers the obtained double-stranded DNA fragment was molecular cloned into the appropriate sites (SalI and SmaI) of the pPLA-1. The obtained plasmid was designated pKLAPLA-5 and comprises the entire preproPLA₂cDNA flanked at the 5'-end by a unique SalI restriction site and at the 3'-end by an XhoI restriction site.

For expression of porcine $PLA_2$ in K.lactis the strong lactase promoter ($P_{LAC}$) of K.lactis is used. Besides for the production of lactase in K.lactis this $P_{LAC}$ promoter sequence was used previously to express in K.lactis bovine chymosin (Berg van den J. et al., 1990, Bio/Technol. 8, 135–139) and human serum albumin (HSA). For the expression of HSA plasmid pGBHSA-20 was constructed and described previously by Swinkels et al. 1993 (Antonie van Leeuwenhoek 64, 187–201).

For expression of HSA in K.lactis the HSAcDNA sequence in pGBHSA-20 is driven by the K.lactis LAC4 promoter. At the 3'-end the HSAcDNA is flanked by LAC4 terminator sequences. In addition, for selection of transformants, pGBHSA-20 contains the Tn5 phosphotransferase gene which confers resistance to the antibiotic G418 (Geneticin, BRL; Reiss et al. (1984) EMBO J. 3, 3317–3322) driven by the S.cerevisiae ADH1 promoter (Bennetzen and Hall (1982) J. Biol. Chem. 257, 3018–3025). In the unique SstII site of the LAC4 promoter pGBHSA-20 contains the E.coli vector pTZ19R which is used for amplification in E.coli. Prior to transformation of K.lactis the E coli pTZ19R sequences are removed from pGBHSA-20 by SstII digestion and agarose gel purification. Transformation of pGBHSA-20 linearized in the SstII site of the LAC4 promoter into K.lactis results in integration into the genomic LAC4 promoter by homologous recombination.

For expression of porcine $PLA_2$ in K.lactis the prepro-$PLA_2$ sequence was fused appropriately to the K.lactis lactase promoter sequence in pGBHSA-20. Thereto pGBHSA-20 was digested with SalI and XhoI and the HSAcDNA sequence was substituted for the SalI-XhoI DNA fragment of pKLAPLA-5 by molecular cloning. As described above this SalI-XhoI DNA fragment of pKLAPLA-5 comprises the preproPLA₂ encoding sequence. The final expression vector for $PLA_2$ was designated pKLAPLA-11.

Yeast transformants were generated by procedures as described in our published patent application EP-A 0 635 574, which are based on the method of Ito H. et al. (J. Bacteriol. 153, 163–168, 1983). pKLAPLA-11 was linearized in the LAC4 promoter by SstII digestion. The pTZ19r sequences were removed by fractionation in and purification from agarose gels. 15 μg's of this DNA fragment were transferred into the K.lactis strains CBS 2360 and CBS 683 and G418-resistant colonies were obtained of both strains after incubation at 30° C. for 3 days.

A limited number of transformants of each host strain were initially selected to test for expression of active porcine $PLA_2$ in the culture medium. Transformants were inoculated in K.lactis YEPD culture medium containing: 1% (w/v) yeast extract; 2% (w/v) peptone; 2% (w/v) glucose and 50 μg/ml G418. After 3 days of growth at 30° C. supernatants were collected and tested for the presence of active $PLA_2$ by the egg yolk activity essay as described below, after treatment of the samples with trypsin. Cleavage of the propeptide is necessary to activate the inactive pro-enzyme (produced by the *K.lactis* transformants) into active, mature $PLA_2$.

All transformants appeared to produce active porcine $PLA_2$ ranging from 5 up to 40 U/ml.

One unit (IU) is defined as the amount of enzyme producing 1 micromole of free fatty acid per minute under standard conditions: egg yolk substrate (0.4% phospholipids), pH 8, 40° C., 6 mM $Ca^{2+}$.

EXAMPLE 2

Production of Stable Enzyme Preparations

Broth of *Kluyveromyces lactis* is subjected to plate filtration followed by ultrafiltration. Ultrafiltrate is treated with 0.3% trypsin at pH 8.0 in the presence of 10 mM $CaCl_2$ during 2.5 hours which results in the removal of the heptapeptide of the pro-enzyme to activate the enzyme.

Benzoic acid and sorbic acid are added as a preservative at pH 4.0 and remaining trypsin activity was inactivated for 30 min. at 70° C. The final product is brownish and contains an activity of 10,000 IU/ml.

Stability of this preparation may be improved by further purification and storage at low temperatures. After one month of storage at 4° C. no loss in enzyme activity is observed.

EXAMPLE 3

Application of Phospholipase A2 in Animal Feed

Trials are carried out with broilers to test the efficacy of phospholipase A2. Male broilers (Ross) are kept from day 1 to day 5 on a standard diet. At day 5, animals are selected from this group and are divided over cages. Weight of the animals and its variation are taken into account. The average weight and its deviation are equal per cage. Fifteen animals are kept in one cage. The cages are situated in an artificially heated, ventilated and illuminated broiler house. Floor space of each cage is 0.98 $m^2$, with wire floors. The broiler house is illuminated for 24 hours per day. During the experimental period, light intensity is gradually reduced. The temperature is gradually reduced from 28° C. during the first week to 23° C. during the last week of the experiment. Humidity in the broiler unit is approximately 60% during the experimental period. Animals have been vaccinated against New Castle disease using the spray method at an age of respectively one and fourteen days. The experiment lasted 33 days comprising a pre-test period of 5 days and a test period of 28 days.

The experimental diets are offered ad lib. to the animals. Water is freely available.

Feed is cold pelleted (temperatures are kept below 65° C.) at a diameter of 3 mm.

The experiment comprises the following treatments:

a) maize/wheat/soya diet (negative control)

b) maize/wheat/soya diet+100 IU/kg c) maize/wheat/soya diet+500 IU/kg

Each treatment is replicated six times (90 birds per treatment in total) Gain and feed conversion are measured. The composition of the feed used is shown in Table 1.

TABLE 1

Composition of maize/wheat/soya diet in experiments with broilers

| Ingredients | Contents (%) |
|---|---|
| Maize | 25.0 |
| Wheat | 15.0 |
| Soy oil | 3.5 |
| Animal fat | 2.0 |
| Manioc | 11.68 |
| Soy flour (50% crude protein) | 19.45 |
| Full fat toasted soy beans | 10.0 |
| Fishmeal | 1.0 |
| Meat meal tankage, high oil | 4.0 |
| Peas | 5.0 |
| Vitamins/mineral premix | 1.0 |
| Limestone | 0.82 |
| Monocalciumphosphate | 1.00 |
| Salt (NaCl) | 0.30 |
| DL-methionine | 0.25 |
|  | 100.00 |
| ME broilers (MJ/kg) | 12.55 |
| Crude protein (%) | 22.1 |
| Crude fat (%) | 9.6 |
| Lysin (available) (%) | 1.23 (1.04) |
| Methionine + Cysteine (available) (%) | 0.91 (0.79) |

Enzyme is added to this diet by mixing it first to a carrier. The results are shown in Table 2.

TABLE 2

Effect of phospholipase A2 in a maize/wheat/soya diet on growth and feed conversion ratio in broilers between 5 and 33 days of age.

|  | Feed intake g | Growth g | Feed conversions ratio |
|---|---|---|---|
| Basal diet | 2613 | 1445 | 1.81 |
| Diet + 100 IU/kg feed | 2569 | 1458 | 1.76 |
| Diet + 500 IU/kg feed | 2526 | 1472 | 1.72 |

An a second experiment, in essence identical to the one described above is performed in which a wheat/rye/soya diet as specified in Table 3 was used as basal diet.

The experiment comprises the following treatments:

a) wheat/rye/soya diet (negative control)

b) wheat/rye/soya diet+100 IU/kg c) wheat/rye/soya diet+500 IU/kg d) wheat/rye/soya diet+1000 IU/kg All other parameters are as described above for the maize/wheat/soya experiment.

TABLE 3

Composition of Wheat/rye/soya diet in experiments with broilers.

| Ingredients | Contents (%) |
|---|---|
| Wheat | 40.0 |
| Rye | 10.0 |
| Soy oil | 1.0 |
| Animal fat | 6.0 |
| Manioc | 4.28 |
| Soya bean meal (45.4% crude protein) | 22.0 |
| Full fat toasted soy beans | 10.0 |
| Meat meal tankage (58 crude protein) | 3.0 |
| Vitamins/mineral premix | 1.0 |
| Limestone | 0.94 |
| Monocalciumphosphate | 1.20 |

TABLE 3-continued

Composition of Wheat/rye/soya diet in experiments with broilers.

| Ingredients | Contents (%) |
|---|---|
| Salt (NaCl) | 0.26 |
| L-lysine HCl | 0.11 |
| DL-methionine | 0.21 |
|  | 100.00 |
| ME broilers (MJ/kg) | 11.9 |
| Crude protein (%) | 21.4 |
| Crude fat (%) | 10.5 |
| Lysin (available) (%) | 1.23 (1.05) |
| Methionine + Cysteine (available) (%) | 0.90 (0.77) |

Enzyme is added to this diet by mixing it first to a carrier. The results are shown in Table 4.

TABLE 4

Effect of phospholipase A2 in a wheat/rye/soya diet on growth and feed conversion ratio in broilers between 5 and 33 days of age.

|  | Feed intake g | Growth g | Feed conversions ratio |
|---|---|---|---|
| Basal diet | 2752 | 1556 | 1.77 |
| Diet + 100 IU/kg feed | 2747 | 1568 | 1.75 |
| Diet + 500 IU/kg feed | 2733 | 1586 | 1.72 |
| Diet + 1000 IU/kg feed | 2724 | 1572 | 1.73 |

As is shown in Table 4, there is an optimum in the range of phospholipase concentrations to be used in this particular broiler diet, i.e. more than about 100 IU/kg feed and less than about 1000 IU/kg of feed. For other systems different optima may exist which can be determined by routine experiments.

EXAMPLE 4

Application of Phospholipase A2 in Milk Replacers

An experiment is performed using 3 groups of each 5 male Friesian Dutch Holstein-Friesian calves.

During the pre-experimental period a commercial milk replacer is fed. After 14 days, animals are divided to receive three treatments, taking weight and variations in weight into account. The animals are kept in individual boxes. The stable is lighted naturally; it is ventilated and is kept at a temperature of about 18° C.

The animals are adapted to their diet during 14 days. Subsequently, faeces is collected quantitatively for 5 consecutive days for 24 hours per day. Calves are harnessed before the experimental period. Faeces is collected in plastic bags attached to the harness. Once a day, faeces is weighed, pooled and stored at −20° C. Prior to analyses, faeces is thoroughly mixed and subsampled.

Animals are fed individually according to their weight following a feeding scheme. The milk replacer used has the following composition:

|  | % |
|---|---|
| Skim milk powder | 58.5 |
| Fat | 19.8 |
| Lactose | 17.6 |
| Starch, vitamins, minerals | 4.1 |
| ME | 4450 kcal/kg |
| Crude protein (N*6.25) | 21.5% |
| Crude fat | 19.5% |

Milk replacer powder is mixed with water before feeding and fed at a temperature of about 40° C.

According to the treatment, the fat consists of 18% beef tallow, coconut fat or lard. Lecithin is added at a concentration of 10% of fat content.

Porcine phospholipase A2 is added to these diets at a final concentration of 500 IU/kg of milk replacer. Digestibility of fat is measured. Results are shown in Table 5.

TABLE 5

The effects of phospholipase A2 treatment on the digestibility of various fats by non-ruminating calves receiving 18% fat in their diets 1.8% lecithin (10% of fat content). Phospholipase A2 is prepared as shown in example 2 and is added to the diet at a final concentration of 500 IU/kg milk replacer.

|  | Without phospholipase A2 | With phospholipase A2 |
|---|---|---|
| Beef tallow | 70.0% | 73.1% |
| Coconut fat | 95.6% | 96.2% |
| Lard | 79.4% | 84.3% |

We claim:

1. An animal feed composition comprising a feed substance for a monogastric or polygastric animal and about 10 to 10,000 IU phospholipase per kg feed, wherein said animal feed composition is suitable for direct consumption, and said phospholipase is provided as phospholipase enzyme included in said animal feed composition as an additive.

2. The composition of claim 1 which further comprises a phospholipid.

3. The composition claim 2 wherein the phospholipid comprises lecithin.

4. The composition of claim 1 wherein the phospholipase is obtainable from a mammal, a plant or a microorganism.

5. The composition of claim 4 wherein the phospholipase is a porcine, bovine, murine, rat, or human phospholipase A2.

6. The composition of claim 1 wherein the phospholipase is obtained by expression of recombinant DNA in a host organism.

7. The composition of claim 6 wherein the host organism is a microorganism selected from the group consisting of bacteria, yeast, and filamentous fungi.

8. The composition of claim 7 wherein the microorganism is selected from the group consisting of Bacillus, Escherichia, Saccharomyces, Kluyveromyces, Hansenula, Pichia, Yarrowia, Candida, Aspergillus, Trichoderma, Penicillium, Mucor, Fusarium and Humicola.

9. The composition of claim 8 wherein the microorganism is *Escherichia coli, Saccharomyces cerevisiae, Kluyveromyces lactis* or *Aspergillus niger.*

10. The composition of claim 2 wherein said phospholipase is present at 1,000 to 5,000,000 International Units per kg of phospholipid.

11. A method to improve the efficiency of feed utilization in a monogastric or polygastric animal, which method comprises feeding said monogastric or polygastric animal a feed composition that comprises a feed substance for said monogastric or polygastric animal and about 10 to 10,000 IU phospholipase per kg feed, wherein said phospholipase is provided as phospholipase enzyme included in said feed composition as an additive.

12. The method of claim 11 wherein said animal is a non-ruminating animal.

13. The method of claim 11 wherein the animal is a calf prior to weaning.

14. A method for promoting the growth of a monogastric or polygastric animal which method comprises feeding said monogastric or polygastric animal a feed composition that comprises a feed substance for said monogastric or polygastric animal and about 10 to 10,000 IU phospholipase per kg feed, wherein said phospholipase is provided as phospholipase enzyme included in said feed composition as an additive.

15. The method of claim 14 wherein said animal is a non-ruminating animal.

16. The method of claim 14 wherein the animal is a calf prior to weaning.

17. A method to produce an animal feed composition for a monogastric or polygastric animal that comprises about 10 to 10,000 IU phospholipase per kg of feed and which is suitable for direct consumption, which method comprises mixing about 10 to 10,000 IU phospholipase per kg of feed substance, wherein said phospholipase is provided as phospholipase enzyme for inclusion in said animal feed composition as an additive.

18. The method of claim 17 which further comprises including in said feed composition at least one phospholipid.

19. The method of claim 17 wherein the phospholipase is produced by recombinant means.

* * * * *